United States Patent [19]

Shimamura et al.

[11] Patent Number: 5,029,574
[45] Date of Patent: Jul. 9, 1991

[54] ENDOSCOPIC BALLOON WITH A PROTECTIVE FILM THEREON

[75] Inventors: Yoshiyuki Shimamura, Matsudi; Kyogo Tsushima, Ryugasaki; Toshihito Seto, Tokyo, all of Japan

[73] Assignees: Okamoto Industries, Inc.; M & M Co., Ltd., both of Tokyo, Japan

[21] Appl. No.: 181,717

[22] Filed: Apr. 14, 1988

[51] Int. Cl.$^5$ .............................................. A61B 1/06
[52] U.S. Cl. ...................................................... 128/6
[58] Field of Search .................... 128/303.1, 395–398, 128/6; 606/13–16

[56] References Cited

U.S. PATENT DOCUMENTS

| | | | |
|---|---|---|---|
| 2,188,736 | 1/1940 | Jordan | 260/746 |
| 3,162,190 | 12/1964 | Del Gizzo | 128/6 |
| 3,417,745 | 12/1968 | Sheldon | 128/6 |
| 3,448,739 | 6/1969 | Stark et al. | 128/658 |
| 4,072,147 | 2/1978 | Hett | 128/6 |
| 4,146,019 | 3/1979 | Bass et al. | 128/6 |
| 4,313,431 | 2/1982 | Frank | 128/7 |
| 4,441,495 | 4/1984 | Hicswa | 604/99 |
| 4,470,407 | 9/1984 | Hussein | 128/398 |
| 4,632,108 | 12/1986 | Gell | 128/207.14 |
| 4,669,465 | 6/1987 | Moore et al. | 128/303.1 |
| 4,784,133 | 11/1988 | Mackin | 128/303.1 |

FOREIGN PATENT DOCUMENTS

| | | |
|---|---|---|
| 0101012 | 2/1984 | European Pat. Off. . |
| 0144132 | 6/1985 | European Pat. Off. . |
| 3406294 | 9/1985 | Fed. Rep. of Germany . |
| 61-173644 | 4/1986 | Japan . |
| 8303188 | 9/1983 | PCT Int'l Appl. . |

Primary Examiner—Max Hindenburg
Attorney, Agent, or Firm—Darby & Darby

[57] ABSTRACT

This invention relates to a balloon and its process which is used in endoscope for observing, diagnosing and curing diseased parts within blood vessel or tubes, a transparent thin film body is provided in forming an inflating portion incorporatedly with an end of a fixing portion wherein the fixing portion is fixed with the end of endoscope, and the transparent thin film body will protect those attachments of endoscope such as lightguide, object glass, optical fiber and the like which are installed in said the end portion of endoscope, wherein it is useful for observation, diagnosis. cure and the like by means of the inflating portion being inflated by injection of physiological salt solution into the interior of inflating portion, in addition a medical laser beam is irradiated so as to be able to cure, that is, the laser beam is transmissible through the balloon itself which is also seeable through.

4 Claims, 4 Drawing Sheets

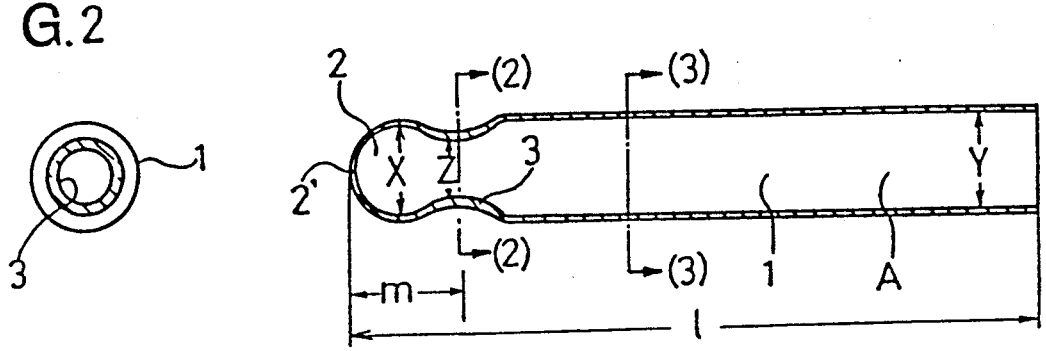
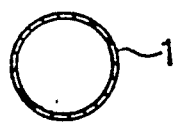
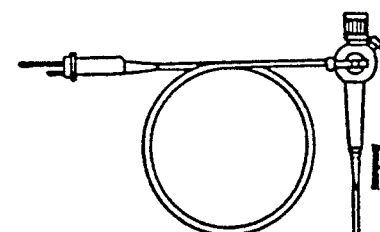
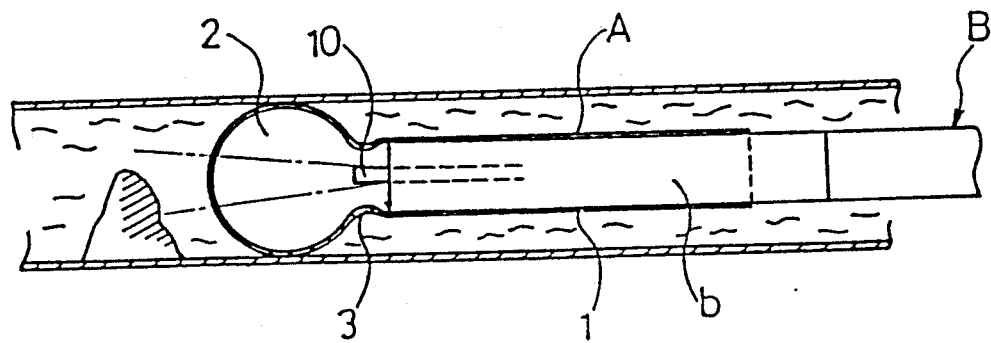

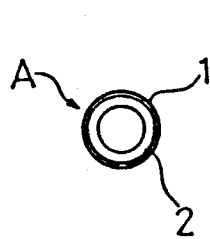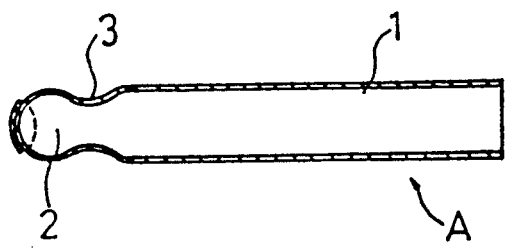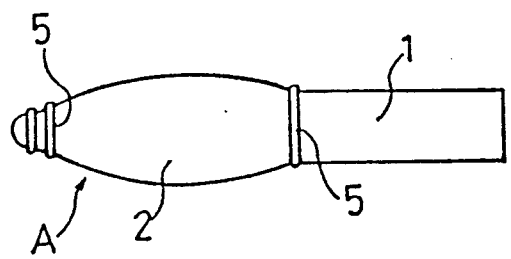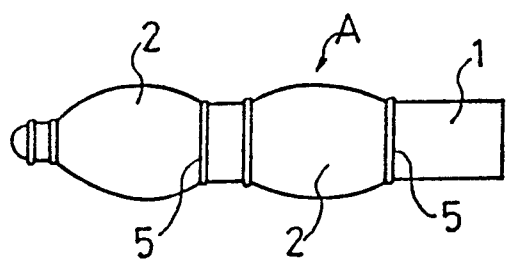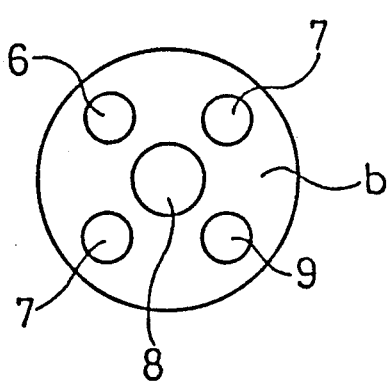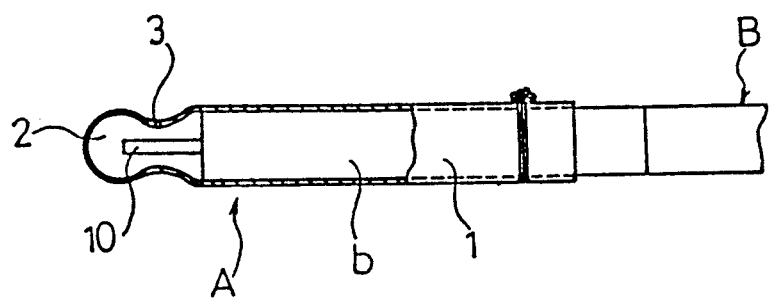

F I G. 16
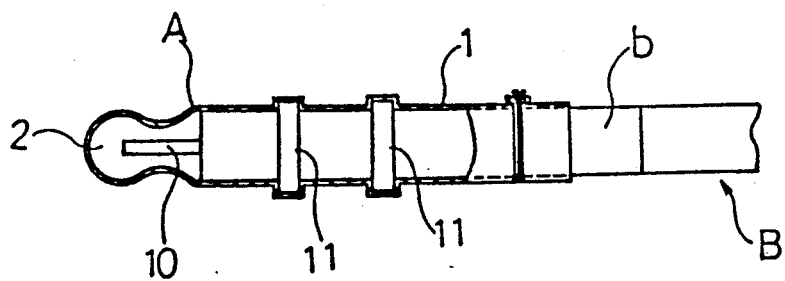
F I G. 17
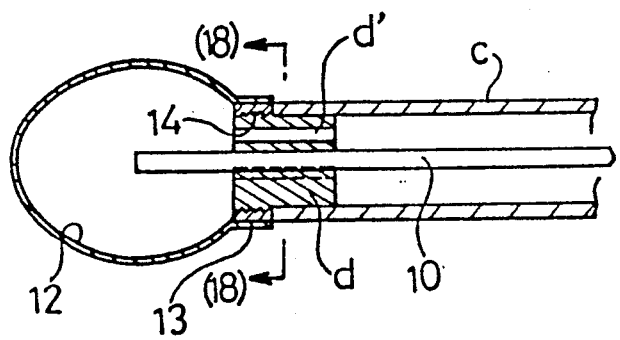
F I G. 18
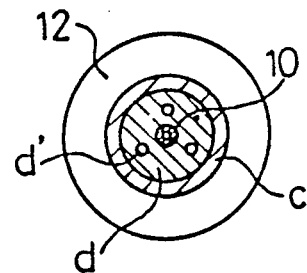
F I G. 19
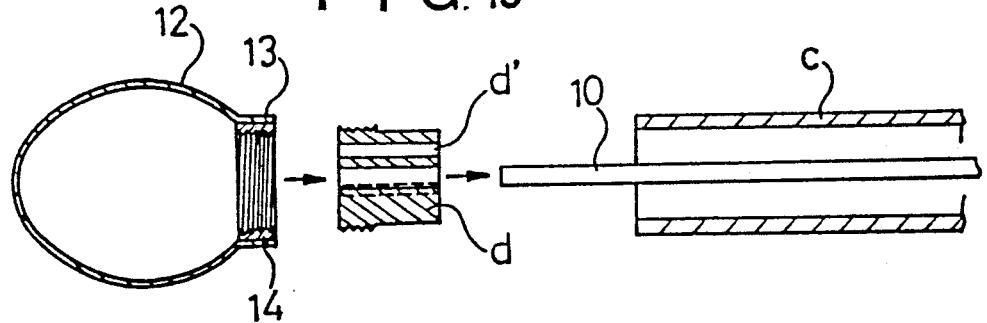
F I G. 20
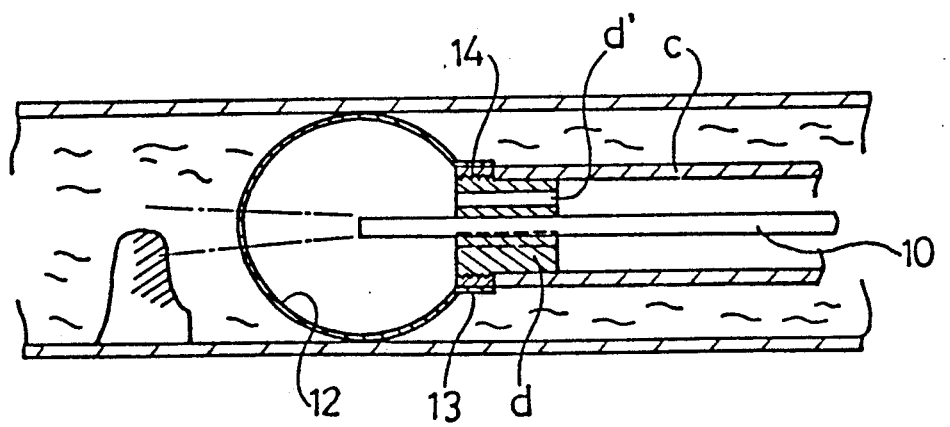

ENDOSCOPIC BALLOON WITH A PROTECTIVE FILM THEREON

This is related to International patent application Ser. No. PCT/JP87/00825, which designated the United States of America.

TECHNICAL FIELD

This invention relates to medical instruments for observing, diagnosing and curing diseased parts within blood vessels or tubes such as the gullet, the stomach, the duodenum, the colon, the nasopharynx, the cystic duct, the abdominal cavity, the bladder, the uterine neck and the like. In particular it relates to instruments of medical treatment by laser beam, i.e., it relates to endoscope or balloon for using optical fiber and the process of producing the same.

TECHNICAL BACKGROUND

When treating some diseased part within blood vessels or internal tube organs by means of laser surgery, the process employed in the prior art involved inserting the endoscope or the optical fiber into the blood vessels or the internal tube organs, and lighting the interior of diseased part by a light-guide which is attached with the end portion of the endoscope for observing or diagnosing the diseased part or internal hemorrhage place through an object lens of the endoscope. After that the laser surgery was treated through the optical fiber which was inserted therein.

However, due to those attachments upon the head such as the light-guide, the object lens and or the optical fiber was exposed upon the top, so that those attachments were easily adhered to and stained by blood, body fluids, foods, sarcomata, secreting fluid and the like. Consequently the diseased parts were often invisible, otherwise, the irradiation of the laser was insufficient. Furthermore due to such an erosion upon the surfaces of attachments causing by the adherence of the above, there was a danger of spoiling the functions of the attachments. Furthermore, when the endoscope is inserted into the blood vessels as a former case, initially one or two other places of the blood vessels used to be cut open excepting an inserting place of the endoscope originally. From the above one or two openings upon them, a disposable type tube catheter for using the blood vessels is inserted into the blood vessels through the above openings to inject an amount of a physiological salt solution through the catheter into the blood vessels in order to inflate the blood vessels with the solution for stopping the flow of blood temporarily, and then the endoscope is inserted from the proper opening.

As to the material of the catheter, it is not transparent, so that one can not look through the tube wall which has not any transillumination of the laser beam.

Further, in the case of general rubber products in transparency, it had a tendency to go down the strength of material because of using a small amount of powder type volcanizing agent or volcanizing accelerater. Therefore, in order to keep the strength of material, it was common to increase the thickness of material whereby it was unable to inflate.

DISCLOSURE OF THE INVENTION

This invention provides a body having a transparent film which forms an inflating portion on the head of fixing portion, fixing the body with on the end portion of the endoscope or the flexible protecting tube of the optical fiber wherein the inflating portion is fixed coveringly and projectedly with into said the end portion, wherein the inflating portion is inflated by means of injecting an amount of the physiological salt solution into the inflating portion which is transilluminative by the laser beam owing to the inflating portion is transparent, whereby according to fix said the body having the thin film with on the end portion of the endoscope, those attachments of the light-guide, the object lens, the optical fiber and the like are protected from the adherences of the blood, the secreting fluid and the like, thus each function will be effective sufficiently.

Further, according to the inflating portion being inflated by means of the physiological salt solution being injected from the ports of supplying an air and an water, a predetermined space is provided, consequently the visual field is widened, whereby the observation and diagnosis or treatment will become easily, and will be performable certainly. Therefore, for example, diagnosis the focuses of thrombus and the like thereto irradiates the laser beam at the focuses, or puts pressure upon the focuses of the gullet varix or upon the focuses around the duodenum wherein checks bleeding from the focuses, otherwise it is possible to widen the strangulated focuses, and cure it.

Further, into the other focuses in each internal organs, irradiates the various laser beams such as YAG (Yttrium, Aluminium, Gallium) laser, Argon laser, Argon dye laser and the like which are transilluminated through the optical fiber thereby checks bleeding or cauterizes the focuses for curing them. Otherwise it is also possible to give an injection of medical fluids into the diseased portion, thus it is useful to provide new treatments.

Further, due to the blood flow being able to stop within the blood vessel, it is neither necessary to operate another opening upon the blood vessel as in the past nor necessary to insert another catheter for stopping the blood flow.

Further, forming the body having the thin film into a globular shaped inflating portion in the same body by means of a dipping process by which it is formed through the waisted portion toward one side of a cylindrically fixed portion.

By making the film thickness of the waist portion thicker than the film thicknesses of the fixed portion and inflating portion thereby, the forming process of said the body is extremely good. Furthermore, the waisted portion displays a strangle-hold-effect during inflation of the globular shaped inflating portion, whereby the inflating portion which is positioned at the end portion of the waisted portion is enabled to be inflated easily.

Moreover, by means of providing such a preventive film for breakdown on the inflating portion as double skins, it is preventive of the breakdown on bursting of the inflating portion caused by picking with the injection needle into the inflating portion when injecting medical, liquids or using the injection needle for medication. Otherwise when using the optical fiber while irradiating the laser beam, even if the inflating portion is broken, still this preventive film can prevent the scattering of the broken pieces within the blood vessel or organs thereon when the inflating portion starts to shrink at last.

This body having the transparent thin film which forms the inflating portion is comprised in that the forming mold of the above is dipped into the composite solution which contains 100 WF (weight fraction) of the rubber content of rubber latex with those additives of 0.7–1.5 FW of powdered vulcanizing agent, 0.2–0.5 FW of powdered vulcanizing accelerater, 0.5–2.0 FW of fluid granulating accelerater and 0.5–2.0 FW of fluid type antioxidant wherein the formed product is dried by vulcanizing pan. Accordingly, such the thin film body having transparency and intensity will be obtainable, furtherly no losing sight of the focuses owing to its transparency, furtherly according to the excellent transmissivity for the laser beam, thus excellent curing effects are shown by the irradiation of the laser beam.

BRIEF DESCRIPTION OF THE DRAWINGS

The accompanying drawings show several embodiments of the practical example of the endoscope or the optical fiber of the invention wherein, FIG. 1 is a longitudinal elevational view, FIG. 2 and FIG. 3 are cross-sectional views respectively along to line (2)—(2) and line (3)—(3), FIG. 4 is a schematic illustration which the thin film body is fixed into the end portion of the endoscope, FIG. 5 is a schematic illustration which the thin film body with the endoscope is inserted into the blood vessel wherein the inflating portion of the body is inflated, FIG. 6 to FIG. 13 inclusively show another practical examples, FIG. 14 is an elevational view of the end portion of the endoscope, FIG. 15 and FIG. 16 are schematic illustrations of another practical examples which the bodies are fixed with the end portions of the endoscopes, FIG. 17 is a longitudinal elevational view in the state of fixing the body into the flexible protective tube for the optical fiber, FIG. 18 is a sectional view along to line (18)—(18), FIG. 19 is a sectional view in the state of disjointing the each parts and FIG. 20 is an enlarged view in the state of inserting the body into the blood vessel wherein the inflating portion is inflated.

DESCRIPTION OF THE PREFERRED EMBODIMENT

Referring now in detail to the drawings as to the several embodiments of the practical examples in the paragraph No. 1 invention and the same No. 2 invention, the body (A) is formed by the transparent thin film having the thickness of 0.10 to 0.40 mm inclusive which consists of the rubber latex, the silicone rubber and the like wherein the inflatable inflating portion (2) having an elasticity is formed incorporatedly with the end of fixing portion (1) which is fixed insertingly with the end portion (b) of endoscope (B) and the body (A) is inserted into the end portion (b) as the inflating portion (2) is projected from the end portion (b).

The fixing portion (1) is a cylindrical shape having the diameters of around 1.0 to 17.0 mm inclusive which the one side end is shaped to be opened, further to which has those shapes in the sectional view of a circle, an oval, a triangle, a square, another polygons and the like as optional shapes, and in compliance with a necessity, those shapes of a projection, a hollow portion, a concavo-concave shaped groove and the like are also applicable to the sectional view, and as another way, providing the inflating portion (2) incorporatedly with wherein the end portion (b) of the endoscope (B) is inserted into within the fixing portion (1) from the aforesaid opened portion so as to project the inflating portion (2) from the end edge of the endoscope (B) wherein the fixing portion (1) which is covered upon the end portion (b) may be tied by those optional means such as the stitches or using a bond for fixing the portion (1). In this case, it is effective to provide the concavo-convave portions of anti-skid upon the outer surface of the end portion (b) in the above.

Figure 6:
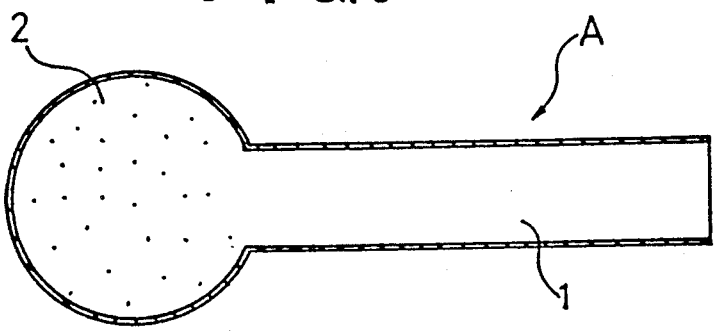
Figure 7:
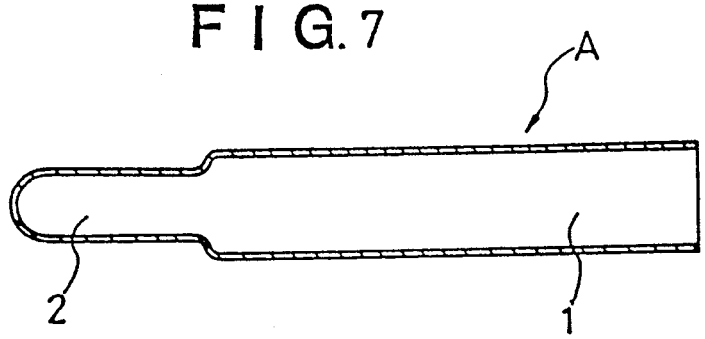

The inflating portion (2) is composed of the globular body having the elasticity which is formed in the end of the fixing portion (1) (FIG. 1 and FIG. 6), or of a projectedly inflated body (FIG. 8), or of a cylindrical body (FIG. 7) thereto, in the case of fixing the body (A) with the end portion (b) of the endoscope (B) coveredly, the body (A) is inflated with a predetermined size by means of the physiological salt solution being injected from the channel of the endoscope which being projected from said the end, or from the air and water supplying orifices thereto, in the shape of prior to the body being inflated, it may be optional as to whether the body (A) is formed with larger diameter than the diameter of fixing portion (1) or not (FIG. 6 and FIG. 8), otherwise formed with mostly same diameter with the fixing portion or not, furtherly formed in combinations with the shape and diameter or not.

Further, the diameters of body (A) may be in 0.9 to 35.0 mm inclusively, that is, it is preferable in compliance with the diagnose and the way of curing, in any way, due to the thickness of the body film becomes more thin causing by means of the inflow of physiological salt solution wherein the body being inflated preferably, the body thin film is not only seeable through sufficiently but also those of YAG laser, the argon laser, the argon dye laser and the like are able to be transilluminated effectively.

Further, the inflating portion (2) has such the function to arrest bleeding from the bleeding portion or the focuses of diseased portion by means of the compression produced by the inflation, wherein to makes the isthmuses of blood vessel such as of the loop blood vessel surrounding the heart to widen thereto, furtherly to contact with the interior wall of the blood vessel fully and closedly by the inflation whereby to block the blood flow.

This thin film of the rubber latex has the excellent elasticity which is composed of transparent thin film with the thickness of 0.10 to 0.40 mm inclusive incorporated with the fixing portion (1) and inflating portion (2) which is dried after adhered the rubber latex to the forming mold having the same shape with the body (A) wherein the mold is dipped into the composed solution so as to face the inflating portion downwardly in which the composed solution consists of: containing 100 FW of the rubber latex with those additives of 0.7–1.5 FW of powered vulcanizing agent, 0.2–0.5 FW of powered vulcanizing accelerater, 0.5–2.0 FW of fluid granulating accelerater and 0.5–2.0 FW of fluid antioxidant thereto, there are some cases where the head portion (2') of inflating portion (2) has a thicker film shape more or less.

Figure 9:
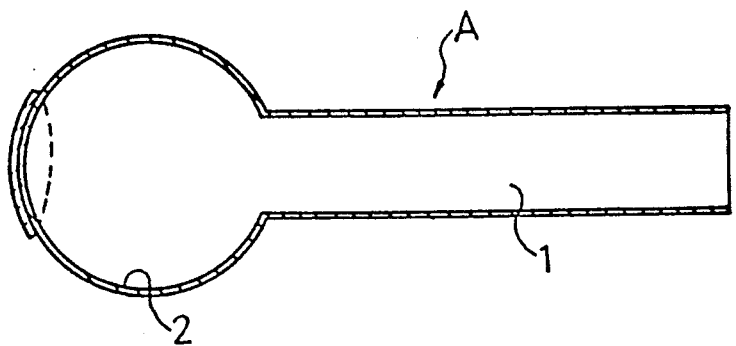

The overall composition of this invention is composed of the transparent thin film body (A) formed incorporatedly with the inflating portion (2) at the end of fixing portion (1) as described before, however, as shown in the paragraph No. 3 invention or the same No. 4 invention, it is able to provide the waisted portion (3) between the fixing portion (1) and the inflating portion (2) (FIG. 1 and FIG. 10), or to provide the preventive film for breakdown (4) with the inflating portion (2) (FIG. 9 and FIG. 10), or to provide both of the waisted portion (3) and the preventive film for breakdown (4) together with as disclosed in the paragraph No. 5 invention (FIG. 10).

That is, the waisted portion (3) is a smaller diameter portion which is formed between the cylindrical fixing portion (1) and the globular shaped inflating portion (2), and which has 75–85% (average 80%) of the diameter against the diameter of fixing portion wherein the film thickness of the waisted portion is formed slightly thicker than the fixing portion and inflating portion.

As shown in FIG. 1, the following tables show the mutual relations of those film thickness, the each interior diameter of (X) (Y) and (Z), the whole length (1) and the length of globular body (m) in the cylindrical fixing portion (1), the globular inflating portion (2), the head portion (2') and the waisted portion (3) wherein the several references are shown hereunder, however, this invention is not restricted by these figures;

| | (Film thickness: m.m.) | | | |
|---|---|---|---|---|
| Examples | (1) | (3) | (2) | (2) |
| No. 1 example | 0.18 | 0.25 | 0.19 | 0.22 |
| No. 2 example | 0.16 | 0.22 | 0.16 | 0.19 |
| No. 3 example | 0.16 | 0.22 | 0.19 | 0.19 |
| No. 4 example | 0.15 | 0.21 | 0.20 | 0.20 |
| No. 5 example | 0.16 | 0.22 | 0.18 | 0.20 |
| No. 6 example | 0.18 | 0.22 | 0.20 | 0.21 |

| | (Inside diameter & length: m.m.) | | | | |
|---|---|---|---|---|---|
| Examples | (Y) | (Z) | (X) | m | l |
| No. 1 example | 1.50 | 1.25 | 1.40 | 1.39 | 10.5 ± 10% |
| No. 2 example | 1.94 | 1.54 | 1.81 | 1.96 | 13.0 ± 10% |
| No. 3 example | 3.00 | 2.46 | 2.85 | 3.16 | 17.0 ± 10% |
| No. 4 example | 5.97 | 4.45 | 5.43 | 5.22 | 26.0 ± 10% |
| No. 5 example | 12.01 | 10.31 | 11.32 | 12.01 | 34.0 ± 10% |
| No. 6 example | 16.92 | 14.01 | 15.26 | 14.81 | 40.0 ± 10% |

The anti-breakdown protective film (4) which is formed in the shape of thin film on the inflating portion (2) is composed that those of synthetic rubbers such as the rubber latex with the same quality of the inflating portion (2) or the silicon rubber, CR, SBR and the like are applied or adhered to the head surface (2') of the inflating portion (2), whereby the protective film (4) has such the specific characters as the excellent adhesive ability to the inflating portion (2) and the elasticity together with the inflating portion (2) without any exfoliation from the base. The position where the protective film (4) is applied or adhered is preferable to the head surface (2') of inflating portion (2), however, if no obstacle is affected into the transmissivity of laser beam through the protective film and the other, the position of adhering the protective film (4) is not always to be limited in the head surface only but more wide range application or adherence of the protective film (4) upon the inflating portion (2) may be applicable and more thicker film may be also applicable.

According to the above described embodiments, even if the inflating portion (2) is broken during treatment, but still the broken pieces is protected from the scattering within the blood vessel for example and whereby the shrinking action is pursuantly actuated by the inflating portion itself.

Figure 8:
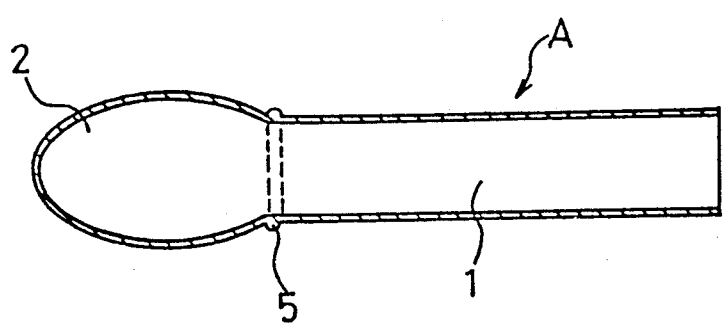

Further, as shown in FIG. 8, FIG. 12 and FIG. 13, it is optional to provide a suitable number of reinforce purposed projective rows (5) or a thicker film portion between the fixing portion (1) and the inflating portion (2), or on the end portion of inflating portion (2), or so as to separate the inflating portion into two parts.

According to the aforesaid embodiments of the thin film body (A) including the cylindrical fixing portion (1), the inflating portion (2), the waisted portion (3), the anti-breakdown protective film (4) and the like, this is why it is so named as the balloon for use of the endoscope which is well-known in the feature and structure in the art of this kind.

The balloon for use of the endoscope which is disclosed in the aforesaid embodiments is fixed into the end portion (b) of endoscope (B) wherein the end portion (b) has an objective lens (6) and two pieces of light-guide (7) (7) (FIG. 14) which illuminate to the visual field through the objective lens, and also has an opening so named as the channel (8) which inserts those of treatable instruments or forceps and another openings such as the air and water supplying port (9), wherein the end portion (b) is possible to move up and down or left and right remotely within the internal organs or blood vessels therein, in the case of the laser beam being irradiated, the optical fiber (10) is inserted into the channels (8) and then the irradiation of laser beam is done. It may be optional to arranged a concavo-concave portion (11) such as a concavo row or concave row upon the outer surface of the end portion (b) for the purpose of anti-skid.

This concavo-concave portion (11) is formed upon the outer surface of end portion of the endoscope (B) with a number of independent or continued concavo rows or concave rows such as a projection or a hollow or a longitudinal row, a transverse row and a ring shape thereby, the shape is optional, wherein it is possible to fix the fixing portion (1) of the balloon coveringly upon the concavo-concave portion so as to fix each others firmly.

Now explaining to the balloon for use of optical fiber of the paragraph No. 6 invention under FIG. 17 to FIG. 20 inclusive, in this case, the inflating portion (12) is formed as same with the aforesaid inflating portion (2) in which the inflating portion (12) is formed as a hollow shape by a transparently elastic thin-film which is composed of the rubber latex or the silicon rubber with the thickness of around 0.10–0.40 mm as the same thickness in the aforesaid inflating portion (2) wherein the inflating portion (12) is inflated by means of injecting the physiological salt solution into the hollow portion of inflating portion (12), whereby according to the inflation, the transmissivity of laser bean is furtherly improved which is irradiated through the optical fiber (10).

As the one of important embodiments in the paragraph No. 6 invention, they are disclosed in FIG. 17 to FIG. 19 inclusively that a fixing ring (14) is fixed within the interior surface of opening portion of the inflating portion (12) wherein the ring (14) is furtherly engaged into a support instrument of fiber tube (d) which is to be fixed detachably into the end portion of the flexible protective-pipe (c).

As shown in the above, the fixing ring (14) is a connecting part to fix the inflating portion (12) into the end of the pipe (c) wherein an inside-screw is threaded within the ring (14) for plugging into the support instrument of fiber tube (d) detachably and the outer surface of the ring (14) is plugged into the opening (13) of inflating portion (12) fixedly by a bond and the like wherein is formed as an incorporated shape with the inflating portion (12).

Those features and structures of the above optical fiber (10) and its flexible protective pipe (c) are well-known in the technical field of the art. Within the flexible protective pipe (c), the optical fiber (10) is inserted passingly through wherein the fiber (10) is possible to transmit the laser beams such as YAG laser, algon laser, algon dye laser and the like, wherein the end of optical fiber (10) is supported by the support instrument (d) where in the end portion of the flexible protective pipe (c). The support instrument (d) is used for supporting the optical fiber (10) in fixing with the interior surface of the end of the flexible protective pipe (c) wherein the thread of a screw is threaded on the outer surface of the end of support instrument (d) for engaging into the inside-screw of the fixing ring (14) wherein a grooves or holes (d') which supplies the physiological salt solution are provided with a suitable number of them within the support instrument (d), wherein an adequate amount of the physiological salt solution is injected into the flexible protective pipe (c) directly or into the channel of the endoscope or further into the air and water supply orifices indirectly wherein the solution is filled up injectingly within the inflating portion (12) through said the pipe (c) and holes (d').

According to the inflation of the above portion (12) by means of injecting the solution, the seeing through is improved furtherly, whereby the transmissivity of those laser beams such as YAG laser, algon laser, algon dye laser and the like will be also improved. Furtherly, by means of the inflation of the portion (12), it is possible to compress around the bleeding portion or focuses, or to widen the isthmuses, or to block the blood flow with contact closely within the blood vessels.

Explaining now in detail to the process of producing the paragraph No. 8 invention, the process of produce is to dip the forming mold into the combined solution which combining a small ratio of the powdered vulcanizing agent and the powdered vulcanizing accelerater with the powdered additive agents being restrained as much as possible, furtherly composing the liquid vulcanizing accelerater and the liquid anti-oxidant, those of all agents are combined with the rubber latex.

As the composition of the combined solution, it consists of 100 FW of the rubber content of the rubber latex which includes those additive agent of 0.8 Fw of the powdered vulcanizing agent, 0.3 FW of the powdered vulcanizing accelerater, 0.7 FW of the liquid vulcanizing accelerater and 1.0 FW of the liquid anti-oxidant, or which includes also those additive agents of 0.7–1.5 FW of, but preferably 0.8–1.2 FW of the powdered vulcanizing agent, 0.2–0.5 FW, but preferably 0.3–0.4 FW of the powered vulcanizing accelerater, 0.5–2.0 FW of the liquid vulcanizing accelerater and 0.5–2.0 FW of the liquid antioxidant.

The purpose of the combination is that adding the vulcanizing agent and vulcanizing accelerater together which are separated originally into the rubber latex, and after agitates them mixingly, furtherly adding the vulcanizing accelerater and the anti-oxidant into the rubber latex mixture in the above, then keeps it within a constant-temperature container with 10°–15° C. for 12–24 hours, furtherly continuously keeps it within the same container with 23°–35° C. for 24–48 hours for accelerating the maturity of combined solution.

The forming mold is so called as the dipping type mold for obtaining the body having a predetermined sized shape wherein this mold is dipped into the aforesaid combined solution for 30–60 seconds after dipped into a coagulating agent preliminarily, after that, the dipped mold is pulled up slowly with thin film of the rubber latex which has around 0.10–0.40 mm of film thickness wherein the adhered film around the mold is heated vulcanizedly with 80°–90° C. for 30 minutes for making a thin film, after that the film is discharged from the mold by using an exfoliate powder and the like. The mold is washed and dried for using again repeatedly.

The thin-film shaped body discharged from the mold is treated by the silicone emulsion for developing the transparency of the thin-film after the washing of the film discharged wherein are dried under 80° C. for 60 minutes, and the mouth of film is cut off with a predetermined length. The transparent thin-film body (A) is a thing which the elastic and inflatable inflating portion (2) is arranged incorporatedly into the end of fixing portion (1) which has a cylindrical shape with approximately 1.0–17.0 mm of inside diameter, and has an opening shape in the one side of the cylindrical shape.

The inflating portion (2) is seeable through from the inside, and by injecting the physiological salt solution from the channel (8) of endoscope (B) or from the air and water supply orifices (9), the transparent inflating portion (2) is inflated to a spherical body or an inflatingly projected body or a cylindrical shaped body which are to be inflated into a predetermined size. In this case aforesaid, it may be optional as to whether it is formed to more larger size in the diameter than the fixing portion, or smaller diameter shape or same diameter shape or not. Furtherly it may be possible to arrange an waisted portion with smaller diameter shape between the inflating portion and fixing cylindrical portion, or reinforcing rings of projected row shape incorporatedly into the same body.

The inside diameter of inflating portion may be selected suitably from between 0.9 mm and 35.0 mm in compliance with the diagnose or the focus to be cured. The thin-film portion of inflating portion (2) becomes more thinly by means of injecting the physiological salt solution into the inflating portion, consequently the seeing through not only becomes more clearly but also the permeability of laser beam will be more improved.

DETAILED COMPOSITIONS

The following are the detailed compositions of basic materials to mold the inflating portion:

| PART I | | |
|---|---|---|
| (1) Natural rubber latex (Poly-1.4-Isoprene) | (rubber part) | 100 FW |
| (2) Vulcanizing agent (colloid Sulphur) | | 0.8 |
| (3) Vulcanizing accelerating aid (Zinc oxide) | | 0.3 |
| (4) Vulcanizing accelerater (Dithio-carbamate compounds) | | 0.7 |
| (5) Anti-oxidant (Paraffine emulsion) | | 1.0 |
| PART II | | |
| (1) Natural rubber lates (Cys-1.4-Poly.isoprene) | (rubber part) | 100 FW |
| (2) Vulcanizing agent (colloid Sulphur) | | 1.2 |
| (3) Powdered Vulcanizing accelerating aid (Zinc oxide) | | 0.35 |
| (4) Vulcanizing accelerater (Dithio-carbamate compounds) | | 0.7 |
| (5) Anti-oxidant (Paraffine emulsion) | | 1.0 |

PROCESS

Preparing an amount of a coagulating agent solution in the normal temperature in which contains 10% of calcium nitrate methanol wherein the forming mold is dipped slowly into the above solution wherein the mold is drawn up slowly again, and removed into the combined solution containing the natural rubber latex mainly for dipping the mold with a coagulating agent solution. After dipping into the above, the mold which a thin latex film is coated around is dried in the vulcanizing oven at 80° C. for 30 minutes. After vulcanizing dry, the thin latex film is peeled off from the mold by using of the exfoliating powder, and the thin latex film, that is, the thin film body (A) is cured within an warm water container at 40°-50° C. for 24 hours in which the water is circulated forcedly within the container for extracting unnecessary contents within the rubber. After the curing within the water, the thin film body (A) is furtherly dipped into the solution containing 10% of silicon emulsion at the normal temperature in order to improve the transparency of the thin film wherein the thin film body (A) is again dried for 60 minutes in 80° C. oven for obtaining an excellent transparent thin film body. The relative sizes of the above body are as follows

| Position | Film thickness (m.m.) | Inside diameter (m.m.) |
| --- | --- | --- |
| Fixing portion | 0.16 | 1.94 |
| Waisted portion | 0.22 | 1.54 |
| Globular shape portion | 0.16 | 1.81 |
| Top surface of inflating portion | 0.19 | |

The transparent thin film body (A) is not restricted in the above relative dimensions, modifications may be made in practicing the invention and the composition modified by the use of different agents, solutions and combinations. Accordingly, it is not intended to have the invention limited to or circumscribed by the specific details of procedure, materials, proportions herein above set forth by way of example in view of the fact that the invention is susceptible to modifications according to individual preference or conditions without departing from the spirit of this disclosure and the scope of the appended claims.

What is claimed is:

1. A balloon for an endoscope, comprising:
a body having an inflatable portion and a fixing portion, at least said inflatable portion being elastic, inflatable and transparent; and
means for preventing scattering of pieces of said inflatable portion which would otherwise take place when said inflatable portion breaks into pieces, said means for preventing scattering including a protective film on at least a part of said inflatable portion, said protective film being outside of said inflatable portion in a path which the pieces would travel in an outward direction when the inflatable portion breaks into pieces, said protective film having a surface which faces an interior of said inflatable portion and is entirely against said inflatable portion.

2. A balloon as in claim 1, wherein said protective film is light transmissible.

3. A balloon as in claim 1, further comprising:
waist means for facilitating inflation of said inflatable portion, said waist means being formed as part of said body and being arranged between said inflatable portion and said fixing portion, said waist means having a wall thickness greater than that of said fixing portion and also greater than that of said inflatable portion.

4. A balloon as in claim 3, wherein said protective film is light transmissible.

* * * * *